US012758240B2

(12) United States Patent
Zickert et al.

(10) Patent No.: US 12,758,240 B2
(45) Date of Patent: Oct. 13, 2026

(54) IMPLANTATION CATHETER AND IMPLANTATION CATHETER ARRANGEMENT FOR HANDLING AN IMPLANT

(71) Applicant: BIOTRONIK SE & Co. KG, Berlin (DE)

(72) Inventors: Christian Zickert, Berlin (DE); Sonja Meine, Berlin (DE); Jan Helge Richter, Berlin (DE); Philipp Konstantin Siegel, Berlin (DE); Jan Romberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 914 days.

(21) Appl. No.: 17/916,173

(22) PCT Filed: Mar. 26, 2021

(86) PCT No.: PCT/EP2021/058036
§ 371 (c)(1),
(2) Date: Sep. 30, 2022

(87) PCT Pub. No.: WO2021/198111
PCT Pub. Date: Oct. 7, 2021

(65) Prior Publication Data

US 2023/0172625 A1 Jun. 8, 2023

(30) Foreign Application Priority Data

Apr. 3, 2020 (EP) .................................... 20167873

(51) Int. Cl.
*A61B 17/22* (2006.01)
*A61B 17/00* (2006.01)
*A61B 17/221* (2006.01)

(52) U.S. Cl.
CPC .................. *A61B 17/22031* (2013.01); *A61B 2017/00867* (2013.01); *A61B 2017/22035* (2013.01);
(Continued)

(58) Field of Classification Search
CPC .............. A61B 17/0485; A61B 17/221; A61B 17/12009; A61B 17/22031;
(Continued)

(56) References Cited

U.S. PATENT DOCUMENTS 9,717,421 B2 8/2017 Griswold et al.
10,737,092 B2 * 8/2020 Shuros ................ A61N 1/3756
(Continued)

OTHER PUBLICATIONS

International Search Report (PCT/ISA/210) and Written Opinion (PCT/ISA/237) mailed on May 31, 2021, by the European Patent Office as the International Searching Authority for International Application No. PCT/EP2021/058036.

*Primary Examiner* — Wesley G Harris
*Assistant Examiner* — Charles W Nichols
(74) *Attorney, Agent, or Firm* — Buchanan Ingersoll & Rooney PC

(57) ABSTRACT

An implantation catheter for implanting an implant into a human or animal body, comprises a first catheter shaft and a holding element being arranged at a distal end of the first catheter shaft, the holding element being configured for holding and releasing the implant. The holding element comprises a shape memory element.

12 Claims, 11 Drawing Sheets

(52) U.S. Cl.
CPC ................. *A61B 2017/2212* (2013.01); *A61B 2017/2217* (2013.01)

(58) Field of Classification Search
CPC .. A61B 2017/00867; A61B 2017/2212; A61B 2017/2217; A61B 2017/22034; A61B 2017/22035; A61B 2050/0085
See application file for complete search history.

(56) References Cited

U.S. PATENT DOCUMENTS

| | | | | |
|---|---|---|---|---|
| 2011/0178535 | A1* | 7/2011 | Whitman ............... | A61B 17/10<br>606/151 |
| 2012/0172892 | A1* | 7/2012 | Grubac ................ | A61N 1/3756<br>606/129 |
| 2013/0253346 | A1 | 9/2013 | Griswold et al. | |
| 2018/0318591 | A1* | 11/2018 | Kabe ...................... | A61N 1/372 |

* cited by examiner

IMPLANTATION CATHETER AND IMPLANTATION CATHETER ARRANGEMENT FOR HANDLING AN IMPLANT

CROSS-REFERENCE TO RELATED APPLICATIONS

This application is the United States National Phase under 35 U.S.C. § 371 of PCT International Patent Application No. PCT/EP2021/058036, filed on Mar. 26, 2021, which claims the benefit of European Patent Application No. 20167873.7, filed on Apr. 3, 2020, the disclosures of which are hereby incorporated by reference herein in their entireties.

TECHNICAL FIELD

The instant invention relates to an implantation catheter as well as to an implantation catheter arrangement comprising such an implantation catheter and an implant. Further, the instant invention relates to a method for handling an implant using such an implantation catheter arrangement.

BACKGROUND

Implantation catheters are well-known. They can be used for delivering implants to an implantation site. Different implantation catheters are available for different implants to be delivered. Furthermore, the implantation catheters are often specifically designed in dependence on the implantation site to be reached by the implantation catheter.

For example, for implanting vascular implants (such as sensory implants) into a pulmonary artery, it is regularly necessary to enter the body of the patient with an implantation catheter by a peripheral venous access and to pass through the right ventricle. Then, a suitable branch of the pulmonary artery may be entered and the implant may be implanted at a suitable implantation site.

In this context, it is a challenge to deliver the implant safely to the implantation site and to release the implant at the implantation site without causing unintended deviations in position. In particular, the implant needs to be fixed reliably to a distal end of the implantation catheter, so as to allow for a safe navigation through the vascular system and the right ventricle to the implantation site. Further, a mechanism for safely releasing the implant at the desired implantation site needs to be provided.

In addition, it may sometimes be necessary to capture an already implanted implant by means of a catheter, such as for the purpose of explantation and/or repositioning of the implant. For example, while an implant is retracted and explanted through the right ventricle and the vascular system, it is mandatory to ensure that the implant does not detach from the catheter.

Known solutions for implanting a pulmonary pressure sensor provide that the implant is attached laterally on the outside of a catheter. In such systems, a wire is used for clamping an anchorage of the implant. In another known system, an implant is released by cutting a thread and then pulling it through a catheter shaft. Further release mechanisms for implants provide a ball jumping out of a loop or use the twisting of undercut structures.

The document U.S. Pat. No. 9,717,421 B2 discloses a kit for intravascular implantation comprising an elongated outer sheath forming an inner lumen with a distal opening, the outer sheath sized to traverse a vasculature of the patient, and an elongated inner sheath with an enlarged distal portion, wherein the enlarged distal portion is configured to substantially fill the inner lumen and close-off the distal opening of the outer sheath. The enlarged distal portion is slidable relative to the outer sheath. The inner sheath further includes a tether with a helical element that is remotely controllable from a proximal end of the inner sheath to release the implantable medical device from a distal portion of the outer sheath.

The known solutions have several drawbacks: For example, an implant that is attached externally to a catheter may be unsafe when guided through the ventricle and chamber. If wires are used, free wire ends can have traumatic effects for the surrounding tissue. The use of threads may lead to unintended knotting or twisting of the threads. In addition, pulling through a thread takes some time and can cause thrombus and entrain air.

Generally, the known solutions require a relatively large catheter shaft size. Their release mechanism is not very defined and may fail in case of jams or narrow structures. Furthermore, once the implant has been released, it can only be captured again with an additional (dedicated) tool.

The present disclosure is directed toward overcoming one or more of the above-mentioned problems, though not necessarily limited to embodiments that do.

SUMMARY

It is an object of the present invention to provide an implantation catheter which facilitates a safe and reliable implantation, reposition and/or explantation of an implant, such as an implantation, repositioning and/or explantation of a vascular implant into/within/from the pulmonary artery.

According to a first aspect, an implantation catheter for implanting an implant into a human or animal body, comprises a first catheter shaft and a holding element being arranged at a distal end of the first catheter shaft. The holding element is configured for holding and releasing the implant and comprises a shape memory element, particularly a pseudoelastic element.

According to a second aspect, an implantation catheter arrangement comprises an implantation catheter according the first aspect and an implant being configured for interlocking with the holding element.

For example, the implant may be a vascular implant, in particular a sensory implant. For example, the implant may comprise a pressure sensor and may be configured for measuring a pulmonary pressure, e.g., within a pulmonary artery. Accordingly, the catheter arrangement may serve for implanting a vascular implant into a pulmonary artery.

For example, the implant may also be a therapeutic implant, particularly an intracardiac therapeutic implant, such as an intracardiac pacemaker.

According to a third aspect, a method for handling an implant inside a human or animal body is presented, wherein an implantation catheter arrangement according to the second aspect is used for at least one of the following: implanting the implant; explanting the implant; and repositioning the implant.

Hence, it is proposed to provide for a mechanism for selectively securing an implant to a distal end of a catheter or releasing the implant from said distal end of the catheter, wherein the releasing is carried out by changing the shape of a shape memory and/or pseudoelastic element. A reliable release and/or capture mechanism for an implant may thus be provided. Furthermore, the shape memory and/or pseudoelastic functionality may allow for a particularly precise actuation of the holding element.

For example, in an embodiment, the holding element is configured for assuming each of a holding state for holding the implant and a release state for releasing the implant, wherein a transition from the holding state to the release state and/or a transition from the release state to the holding state is supported by means of the shape memory of the shape memory element.

In a preferred embodiment, the shape memory and/or pseudoelastic element comprises a loop, such as a wire loop. For example, the shape memory and/or pseudoelastic element may comprise or consist of a nitinol wire. Such a nitinol wire may be pre-formed (e.g., by annealing) in a shape, which may correspond to one of the holding state and the release state mentioned above.

In an alternative embodiment, the shape memory comprises at least one tine, e.g., shaped as a barb, claw or hook.

In further alternative embodiment, the shape memory comprises a stent or stent-like structure.

In a variant, when the distal end of the first catheter shaft points in a first direction, an overall extension of the holding element in a second direction that is perpendicular to the first direction is larger in the holding state than in the release state. Thus, in the holding state, the holding element may, for example, be configured for interlocking with one or more element provided in the implant so as to secure the implant to the distal end of the first catheter shaft, preferably with one or fixation elements, such as fixation loops, which are configured to arrange and/or secured the implant at the intended implantation site. Alternatively, the holding element may, for example, be configured for interlocking with one or more undercuts or one or more slots provided in the implant so as to secure the implant to the distal end of the first catheter shaft. Further, in the release state, the shape memory portion may be completely retracted in the first catheter shaft.

Further, in an embodiment, the first catheter shaft comprises an actuation element that may be actuated at a proximal end of the first catheter shaft for deforming the shape memory element. Hence, a transition between the holding state and the release state may be induced by actuating the actuation element, e.g., by a surgeon.

In an embodiment, the actuation element may extend inside a first lumen of the first catheter shaft, such as from the proximal end of the first catheter shaft to the distal end of the first catheter shaft. For example, a manual actuation device, such as a switch that is operably connected with the actuation element, may be integrated in a handle that is arranged at a proximal end of the implantation catheter.

It is also within the scope of the present invention that the implantation catheter may comprises a second catheter shaft (which may be referred to as outer catheter shaft) including a second lumen, wherein the first catheter shaft (which may also be referred to as inner catheter shaft) may be at least partially guided inside said second lumen.

In an advantageous variant, a distal end of the second catheter shaft comprises a protective sleeve, the protective sleeve being configured for receiving the implant. The implant may be housed inside the protective sleeve and secured to the distal end of the inner catheter shaft by means of the holding element while being navigated through the human or animal body to the desired implantation site.

Thus, a secure transfer of the implant through the vascular system and the heart of the patient may be facilitated. In particular, in this variant, the implantation catheter as a whole (i.e., the inner catheter shaft, the outer catheter shaft, the holding element including the actuation mechanism, and the protective sleeve) may have a relatively thin cross-section. As a result of such a design, the vessels and heart valves may be protected during the implantation. The risk of embolism or infection may thus be reduced. Further advantages are a reduction of implantation times and more generally a simplified implantation process for the implantation of a pressure sensor into the pulmonary artery, so that even relatively inexperienced implanters can implant the system easily and safely.

In an embodiment, a pushing element may be arranged at the distal end of the first catheter, the pushing element being configured for pushing the implant out of the implantation catheter, e.g., out of the protection sleeve. For example, a proximal portion of the implant may rest against the pushing element while the implant is secured to the inner catheter shaft by means of the holding element.

In an embodiment of the third aspect, the method for comprises the following steps: a) guiding the implant to a desired implantation site while the implant is attached to the distal end of the first catheter shaft by means of the holding element; and b) releasing the implant at the desired implantation site by changing the shape of the shape memory element.

In another embodiment of the third aspect, the method for comprises: c) guiding the distal end of the first catheter shaft to the implanted implant; and d) attaching the implant to the distal end of the first catheter shaft by changing the shape of the shape memory element.

Hence, in an embodiment, the implantation catheter may be able to carry out both of the following functions: Releasing an implant at an implantation site; and capturing an implant inside the human or animal body, e.g., for the purpose of repositioning or explantation of the implant. Advantageously, material and time may thus be saved, since a separate (dedicated) tool form repositioning or explantation is not necessary.

All aspects and features of the embodiments described above and in the following can be combined with each other unless explicitly stated otherwise.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein, FIGS. 1A-E each schematically and exemplarily illustrate a section of a longitudinal cross-section of an implantation catheter arrangement in accordance with one or more embodiments.

DETAILED DESCRIPTION

Figure 1A:
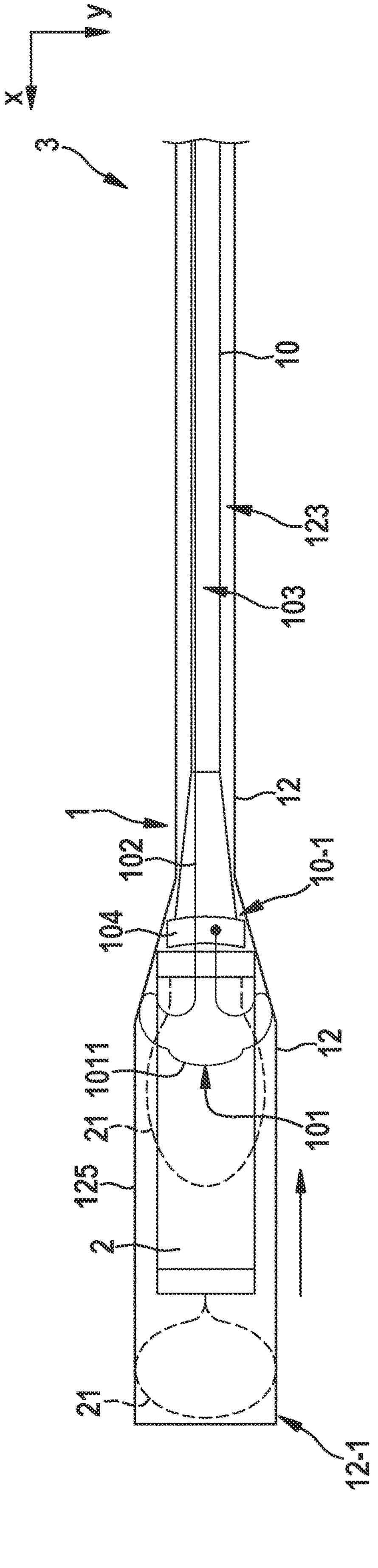

FIG. 1A shows a section of a longitudinal cross-section of an implantation catheter arrangement 3 in accordance with one or more embodiments. In the exemplary embodiment of FIG. 1A, the implantation catheter arrangement 3 comprises an implantation catheter 1 and an implant 2 that is attached to a distal section of the implantation catheter 1. For example, the implant 2 may be a sensory implant. For example, the implant 2 may comprise a pressure sensor and may be configured for measuring a pulmonary pressure, e.g., within a pulmonary artery of a patient. Accordingly, the catheter arrangement 3 may serve for implanting a vascular implant 2 into a pulmonary artery.

The implantation catheter 1 comprises a first catheter shaft 10, which may also be referred to as an inner catheter (shaft), and a second catheter shaft 12, which may also be referred to as outer catheter (shaft). The outer catheter shaft 12 comprises a second lumen 123, in which the inner catheter shaft 10 is (at least partially) movably guided.

A distal end 12-1 of the outer catheter shaft 12 comprises a protective sleeve 125, which is configured for receiving the implant 2. In the situation depicted in FIG. 1A, the implant 2 is entirely housed within the protective sleeve 125. For example, this configuration may be referred to as a transport configuration, in which the implant 2 may be navigated through the vascular system and/or the heart of the patient. In the transport configuration, the implant 2 is attached to a distal end 10-1 of the first catheter shaft 10 by means of a holding element 101.

In the present exemplary embodiment, the holding element 101 is provided in the form of a wire loop 101. The wire loop 101 engages with one or more portions of the implant 2 so as to hold the implant 2 inside the protective sleeve 125. In other words, the implant 2 is configured for interlocking with the holding element 101. Preferably, the wire loop engages with one fixation 21 loop of the implant 2 at the proximal end, wherein the fixation loop at the proximal end of the implant and also the fixation loop at the distal end of the implant may also be made of nitinol with a set shape. Alternatively, the wire loop may engage with other elements, such as slots, undercuts or hitches of the implant 2.

In the transport configuration, a proximal end of the implant 2 may rest against a distal end 10-1 of the first catheter shaft 10. For example, a pushing element 104 may be arranged at the distal end 10-1 of the first catheter shaft 10, wherein the proximal end of the implant 2 may rest against said pushing element 104, as illustrated in FIG. 1A.

The pushing element 104 is configured for pushing the implant 2 out of the implantation catheter 1 as a result of a relative (longitudinal) movement of the first catheter shaft 10 with respect to the second catheter shaft 12. Specifically, the implant 2 may thus be pushed out of the protective sleeve 125 at a desired implantation site.

The holding element 101 is configured for releasing the implant 2, such that the implant 2 may be pushed out of the protective sleeve 125. In other words, the holding element 101 is configured for selectively holding and releasing the implant 2. Specifically, the holding element 101 may be configured for selectively assuming each of a holding state for holding the implant 2 and a release state for releasing the implant 2. FIG. 1A exemplarily shows the holding state of the holding element 101. The release state of the holding element 101 is shown in FIGS. 1D and 1E, for example, which will be referred to further below.

The holding element 101 comprises a shape memory element 1011. For example, the shape memory element 1011 may include at least a loop section of the holding element 101 that is configured to engage with the implant 2, as exemplarily illustrated in FIG. 1A. For example, the shape memory element 1011 may be pre-formed in a configuration such as the one depicted in FIG. 1A, which may corresponds to the holding state of the holding element 101. Hence, a transition of the holding element 101 from the release state to the holding state may be supported by the shape memory functionality of the shape memory element 1011. Alternatively, in other embodiments, the shape memory element 1011 may be pre-formed a configuration corresponding to the release state, such that a transition from the holding state to the release state is supported by the shape memory.

In an exemplary embodiment, the holding element 101 may at least partially consist of a thin nitinol (nickel titanium) wire. For example, at least a portion of the nitinol wire may have been pre-formed or shape set by annealing so as to form the loop depicted in FIG. 1A. As a result, in the absence of external forces exerted on the nitinol wire, the holding element 101 will automatically (re-)assume its holding position, as illustrated.

For releasing the implant 2, the surgeon may change the shape of the shape memory element 1011 by means of an actuation element 102, which may be actuated at a proximal end of the catheter 1. For example, to this end, an actuation device, e.g., in the form of a switch, may be integrated in a handle at a proximal end of the catheter 1 (not illustrated).

In accordance with the exemplary embodiment of FIG. 1A, the actuation element 102 may comprise at least one free end (or leg) of the wire that forms the holding element 101. For example, the first catheter shaft 10 may comprise a first lumen 103, in which said actuation element 102 (in the form of at least one leg of the wire forming the holding element 101) is guided from the distal end 10-1 to the proximal end of the catheter shaft 10. Specifically, in the embodiment of FIG. 1A, one leg of the wire forming the holding element 101 is attached to the pushing element 104 at the distal end 10-1 of the first catheter shaft 10, whereas the other leg is guided through the first lumen 103 from the distal end 10-1 to the proximal end of the first catheter shaft 10.

In the following, several steps of a release procedure of the implant 2 will be explained with reference to FIGS. 1A-E.

Once the implant 2 has been guided to the desired implantation site by means of the catheter 1, the outer catheter 12 is retracted with respect to the inner catheter 10 so as to expose the implant 2. This movement of the outer catheter 12 is indicated in FIG. 1A by means of a thick arrow pointing to the right. Alternatively, the outer catheter 12 may also remain at a defined position, and the inner catheter 10 with fixation etc. could be advanced (e.g., in case of the implant 2 is an intracardiac pacemaker).

Figure 1B:
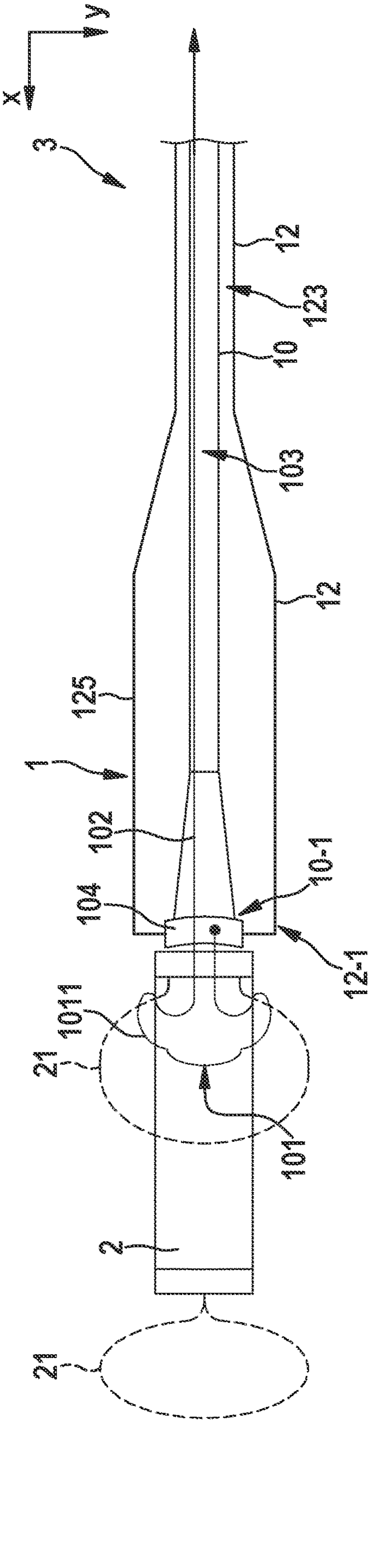

As a result of this step, the implant 2 is no longer housed in the protective sleeve 125, as illustrated in FIG. 1B. When the implant 2 leaves the protective sleeve 125, fixation loops 21 that are arranged at a proximal end and at a distal end of the implant 2 may expand so as to anchor the implant 2 in the surrounding tissue. It should be noted that in the situation depicted in FIG. 1B, the implant 2 is still secured to the distal end 10-1 of the inner catheter 10 by means of the holding element 101.

For releasing the implant 2, the shape memory element 1011 may be actively deformed by actuating the actuation element 102, i.e., by pulling at the proximal end of the wire forming the holding element 101. This is schematically indicated in FIG. 1B by means of an arrow pointing to the right. The other end of the holding element 101 not to be pulled may be fixed to the actuation element 102.

Figure 1C:
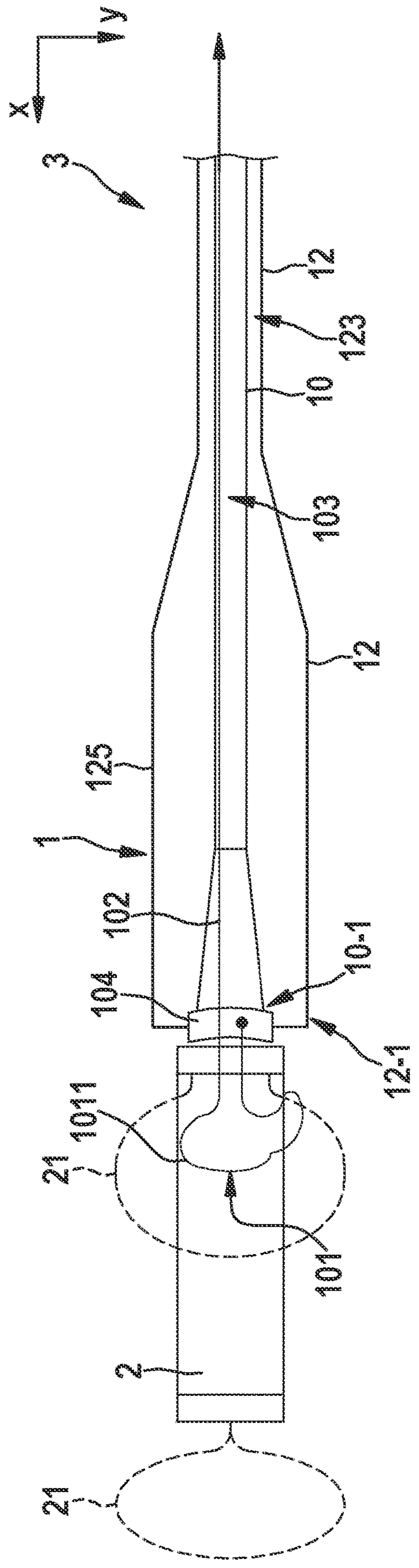
Figure 1D:
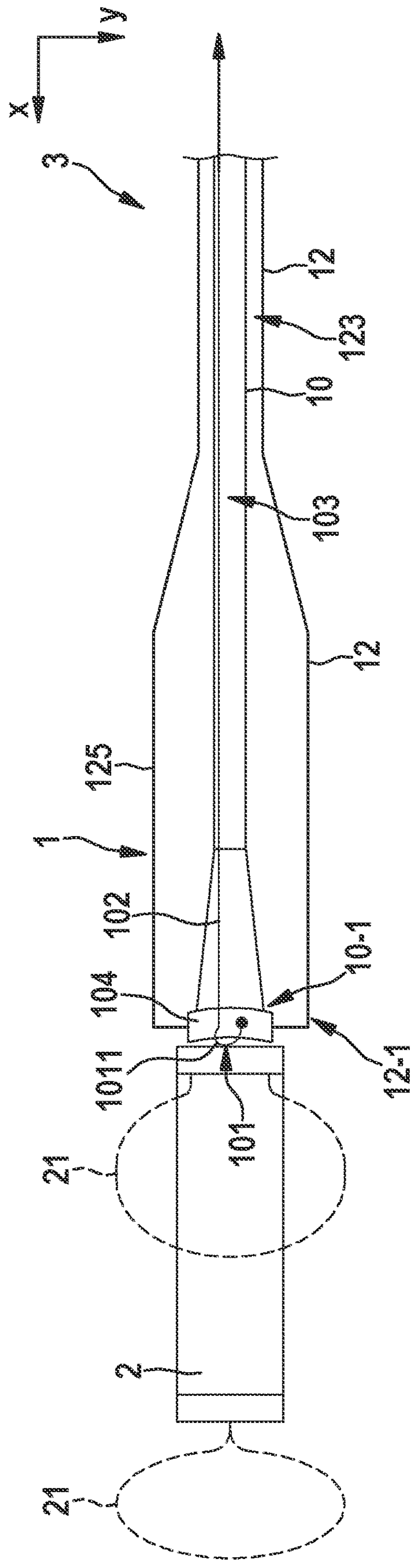
Figure 1E:
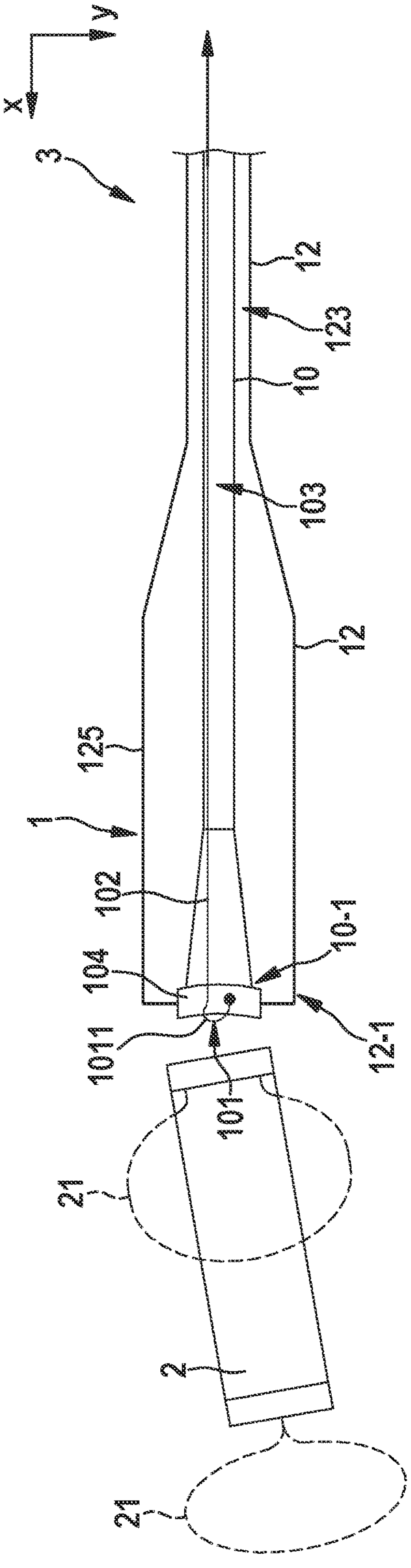

In FIG. 1C, an intermediate state during a transition from the holding state to the release state of the holding element 101 is shown. FIG. 1C illustrates the asymmetric deformation of the shape memory element 1011, which results from the activation of the actuation element 102, i.e., the pulling of the wire end 102 to the right.

If the proximal end of the wire is pulled further in the proximal direction indicated by the arrow, the holding element 101 is further deformed until it assumes its release state. The release state is illustrated in FIG. 1D. In the release state, the holding element 101 no longer engages with the implant 2. Hence, the implant 2 can completely detach from the distal end 10-1 of the inner catheter 1, as illustrated in FIG. 1E.

It should be noted that, when the distal end 10-1 of the first catheter shaft 10 points in a first direction X, as illustrated in each of FIGS. 1A-E, an overall extension of the holding element 10 in a second direction Y that is perpendicular to the first direction X is larger in the holding state (see FIG. 1A) than in the release state (see FIG. 1E). For example, the relatively large overall extension of the holding element 101 in the second direction Y in the holding state may facilitate an interlocking with the implant 2. E.g., in the holding state, one or more portions of the wire loop comprising the shape memory element 1011 may engage with a fixation loop 21 arranged or fixed at the proximal end of the implant 2 so as to interlock with the implant. In the release state, such an interlocking may not be possible as a result of the smaller extension of the holding element 101 in the second direction Y.

As further illustrated in FIGS. 1A-B, in the holding state, the shape memory element 1011 of the holding element 101 may form an undercut, which may engage, e.g., with one fixation loop 21 arranged or fixed at the proximal end of the implant 2 so as to interlock with the implant 2. In the release state, the undercut may vanish or maybe less pronounced, such that an interlocking with the implant 2 is not possible.

Figure 2A:
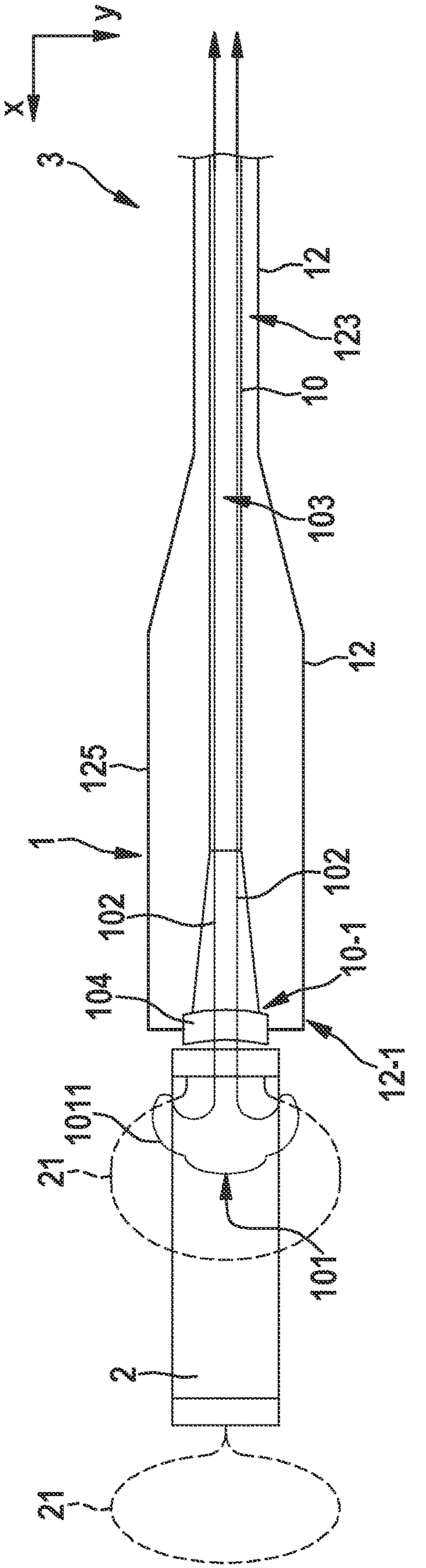
FIGS. 2A-C each schematically and exemplarily illustrate a section of a longitudinal cross-section of an implantation catheter arrangement in accordance with one or more embodiments.
Figure 2B:
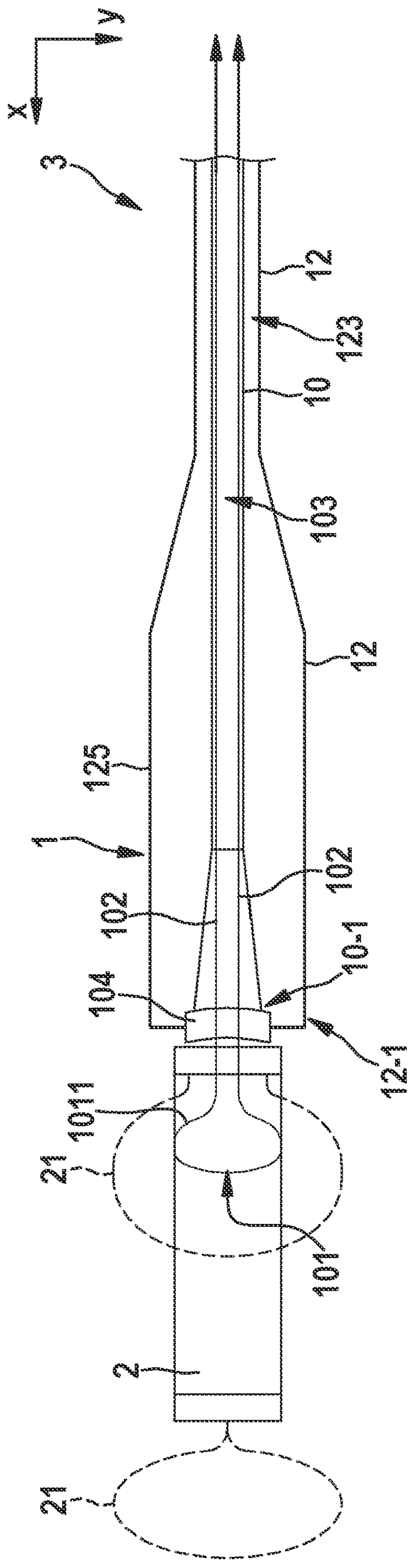
Figure 2C:
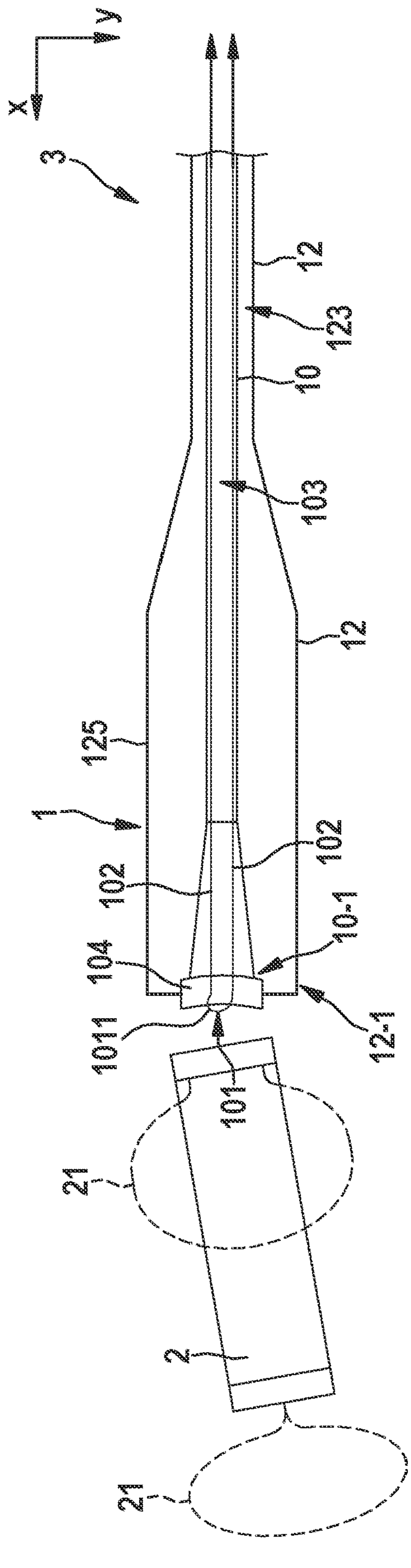
Figure 3A:
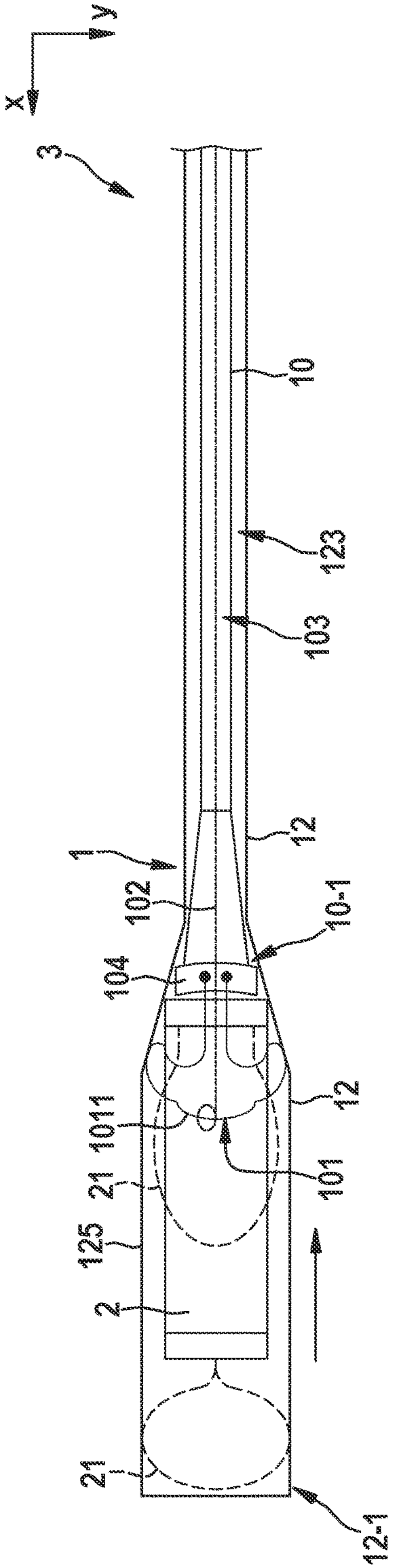
FIGS. 3A-D each schematically and exemplarily illustrate a section of a longitudinal cross-section of an implantation catheter arrangement in accordance with one or more embodiments.
Figure 3B:
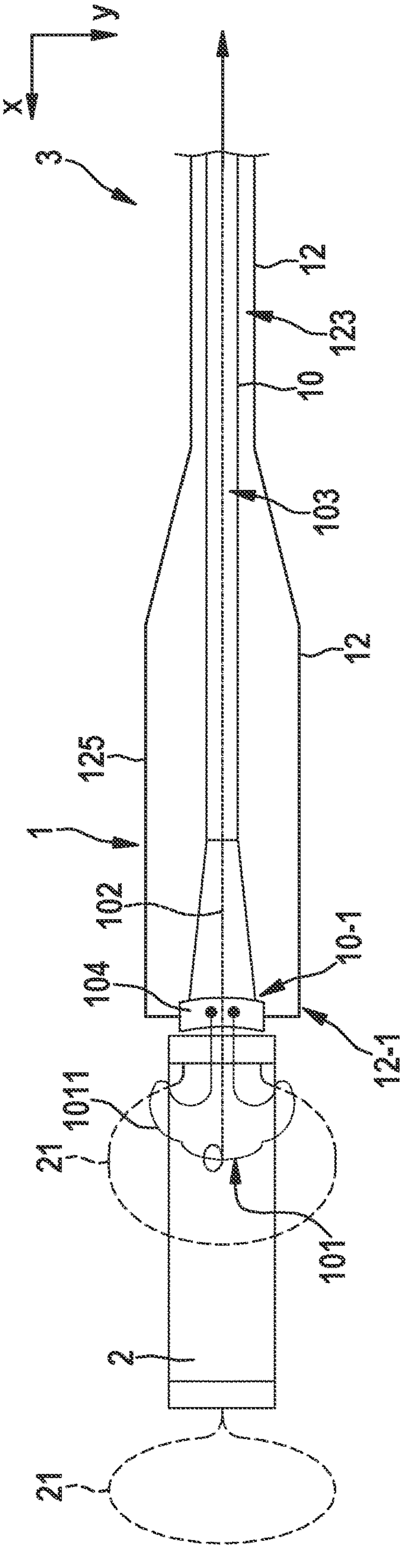
Figure 3C:
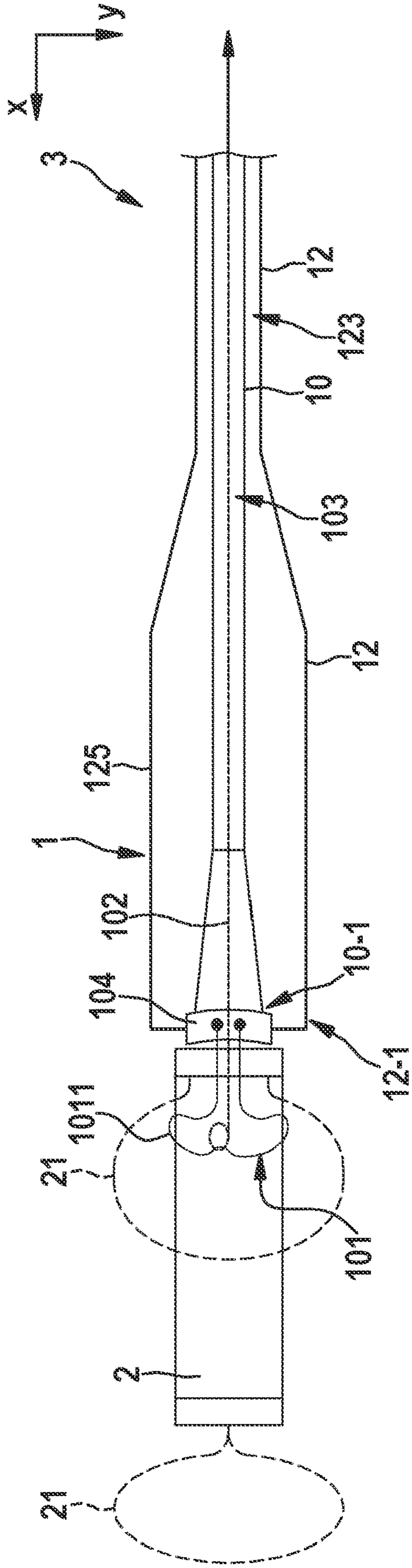
Figure 3D:
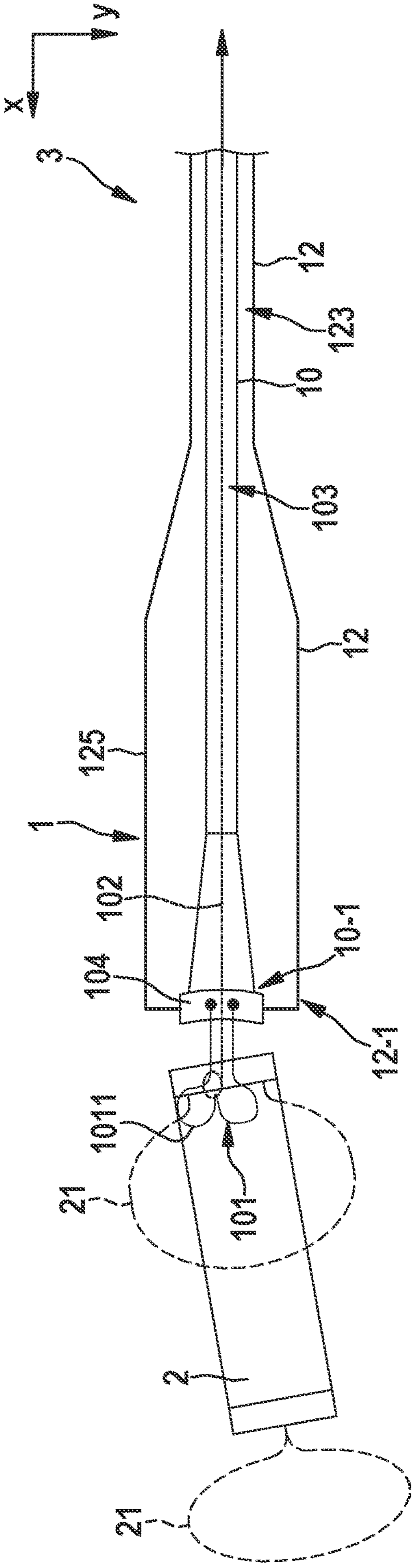
Figure 4A:
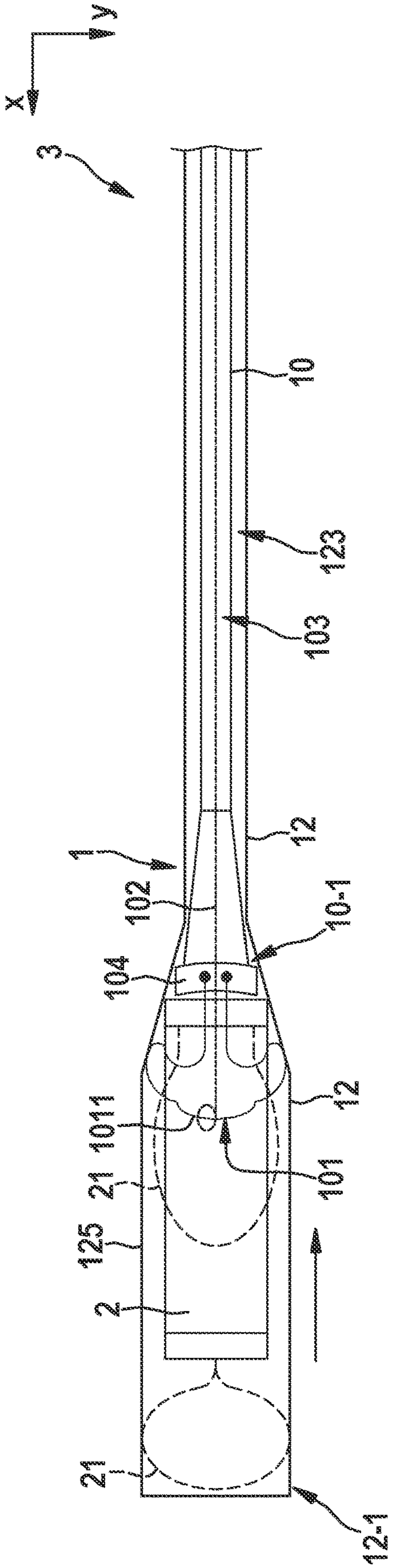
FIGS. 4A-D each schematically and exemplarily illustrate a section of a longitudinal cross-section of an implantation catheter arrangement in accordance with one or more embodiments.
Figure 4B:
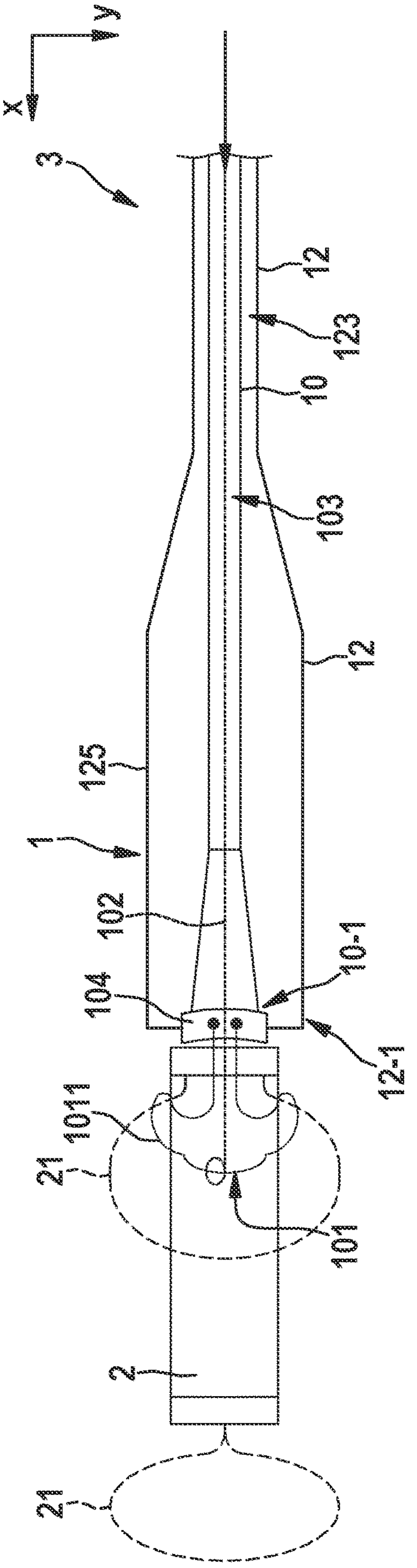
Figure 4C:
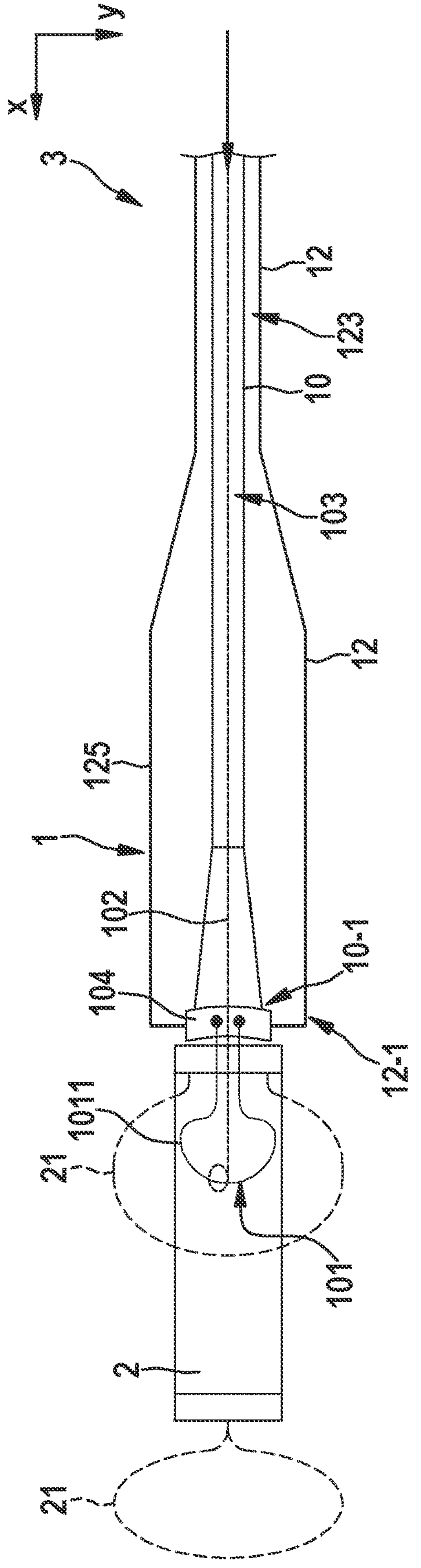
Figure 4D:
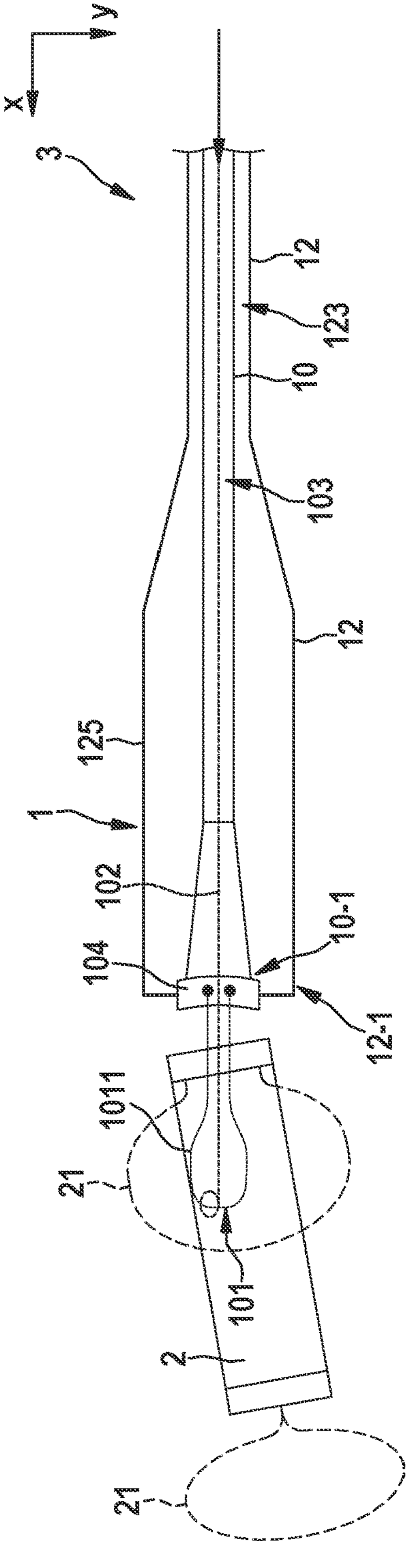

FIGS. 2A-C shows another embodiment of the implantation catheter 1. The basic structure of the implantation catheter 1 according to this embodiment is similar to the embodiment of FIGS. 1A-E, the only difference consisting in the design of the actuation element 102. In this embodiment, both legs of the wire forming the holding element 101 are guided through the first lumen 103 to the proximal end of the inner catheter 10 and thus form part of the actuation element 102. This is to say that both legs of the wire may be pulled towards the proximal end for bringing the holding element 101 from the holding state (see FIG. 2A) into the release state (see FIG. 2C). This is schematically indicated by two arrows pointing to the right in FIGS. 2A-C. As a consequence, as illustrated in FIG. 2B, which depicts an intermediate state during the transition from the holding state to the release state, the shape of the shape memory element 1011 is continuously changed in a symmetric way.

FIGS. 3A-D shows yet another variant embodiment of the implantation catheter 1. In this variant, both legs of the wire loop forming the holding element 101 are attached at the distal end 10-1 of the inner catheter 10. An actuation element 102 is provided in the form of a separate (dedicated) actuation wire, which is guided through the first lumen 103. The actuation element 102 is attached by means of an attachment loop to a central portion of the shape memory element 1011. In principle, the release procedure for the implant 2 is carried out in a similar fashion as explained above with reference to FIGS. 1A-E, namely, by pulling a proximal end of the actuation wire 102 towards the proximal end of the catheter 1 (see arrows to the right in FIGS. 3B-D). The formation of the holding element 101 occurs in a symmetric manner as a consequence of the central attachment of the actuation wire 102 to the shape memory element 1011.

The embodiment illustrated in FIGS. 4A-D is similar to the one of FIGS. 3A-D in that it also comprises a dedicated actuation wire 102. However, in contrast to the previous embodiment, in the embodiment of FIGS. 4A-D, the release procedure is carried out by pushing (instead of pulling) the actuation wire 102 towards the distal end 10-1 of the inner catheter 10 (see arrows pointing to the left in FIGS. 4B-D), thereby deforming the shape memory element 1011, such that it assumes a shape having a smaller overall extension in the second direction Y.

Figure 5A:
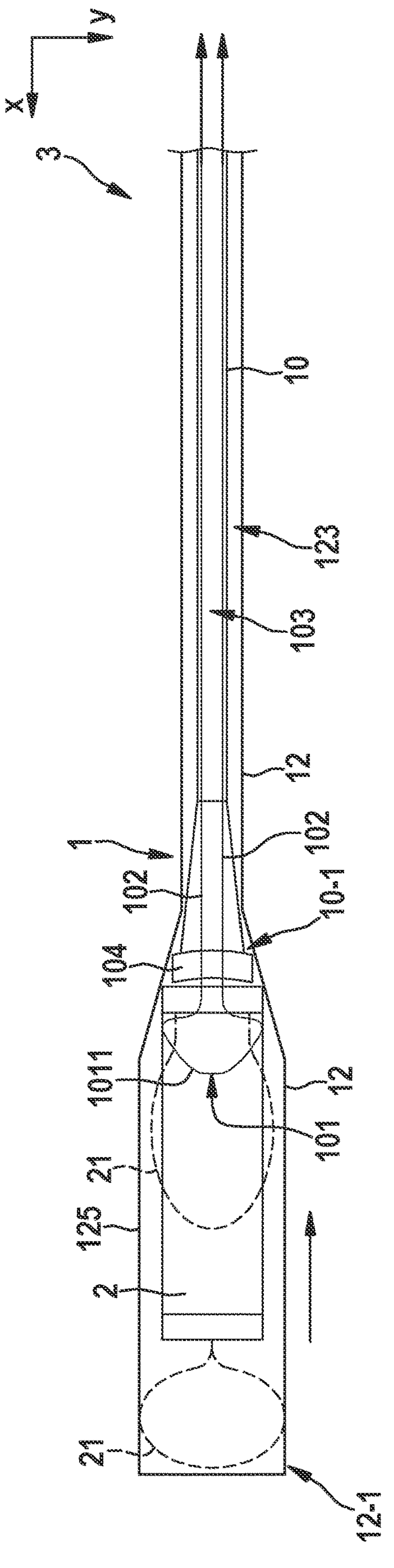
FIGS. 5A-C each schematically and exemplarily illustrate a section of a longitudinal cross-section of an implantation catheter arrangement in accordance with one or more embodiments.
Figure 5B:
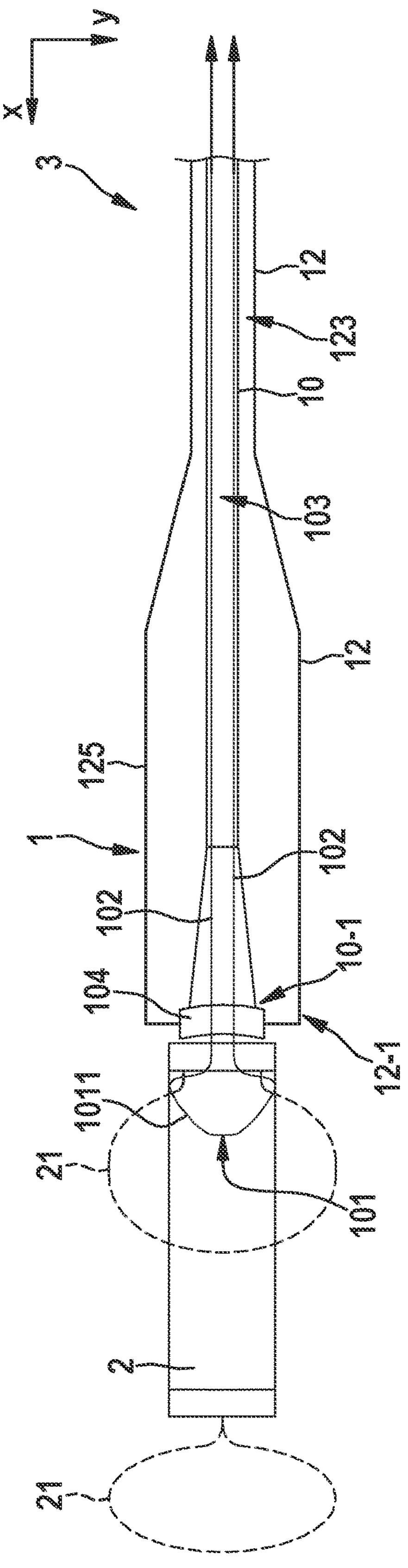
Figure 5C:
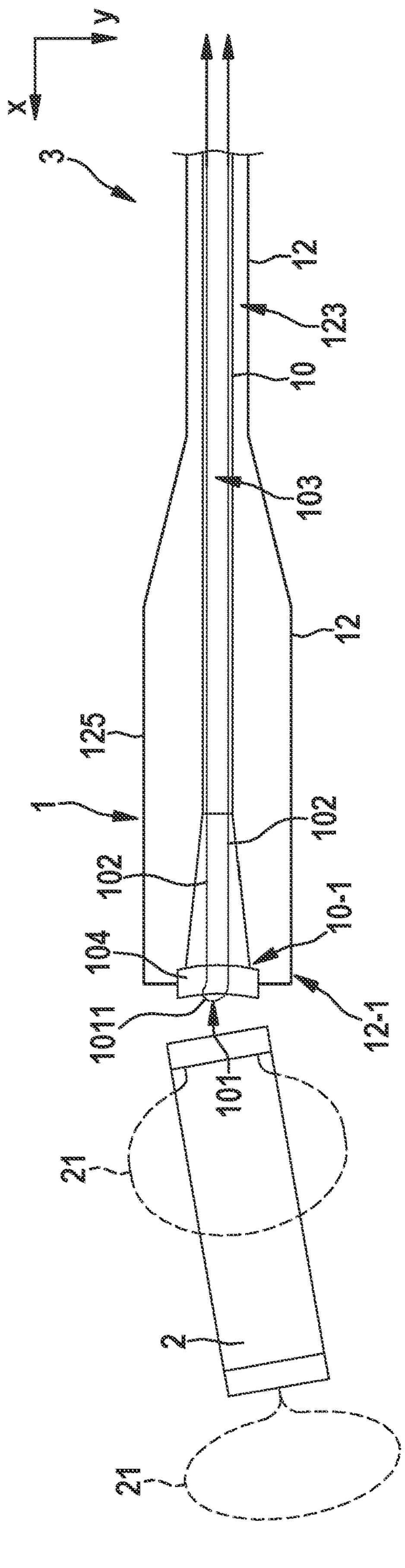

FIGS. 5A-C illustrates yet another exemplary embodiment of an implantation catheter 1. Similar to the embodiment explained above with reference to FIGS. 2A-C, the actuation element 102 comprises both legs of the wire loop forming the holding element 101. Thus, a transition from the holding state to the release state may be initiated by pulling both wires 102 towards the proximal end of the inner catheter 10.

Figure 6A:
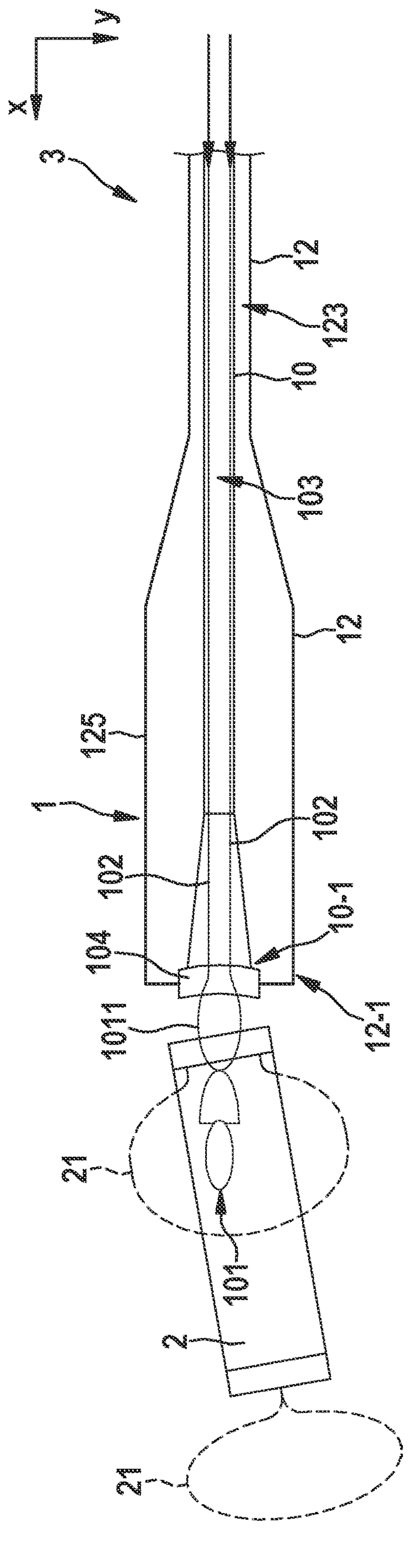
FIGS. 6A-C each schematically and exemplarily illustrate a section of a longitudinal cross-section of an implantation catheter arrangement in accordance with one or more embodiments.
Figure 6B:
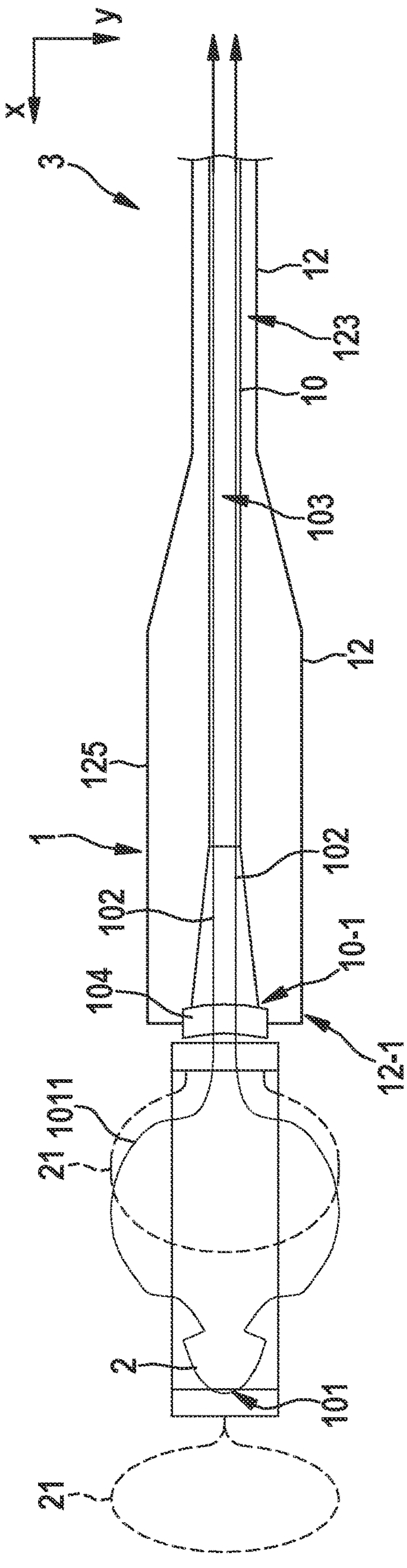
Figure 6C:
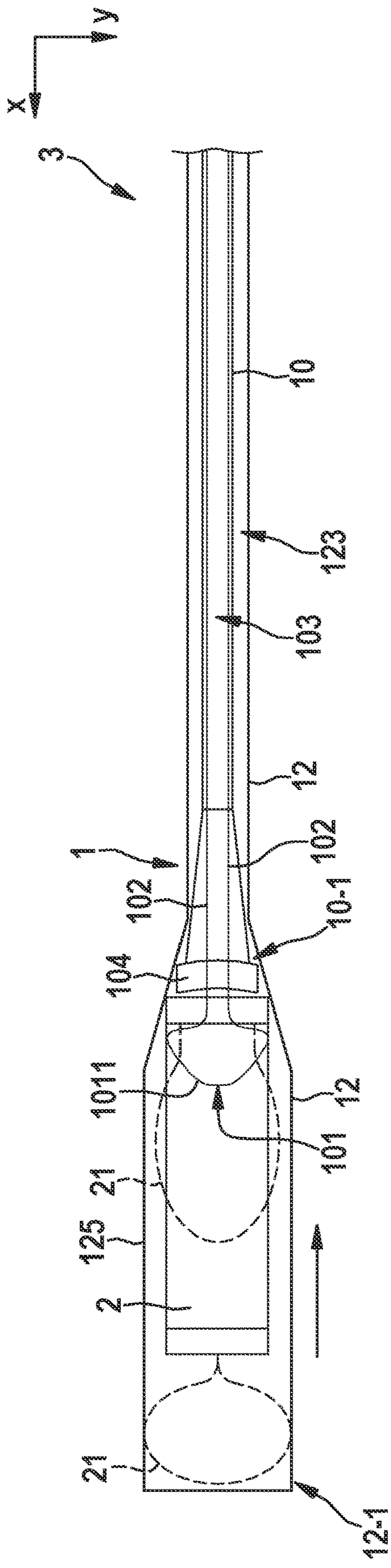

FIGS. 6A-C show different stages of a capture procedure carried out with the implantation catheter 1 of FIGS. 5A-C. For example, the catheter 1 may be used for explanting or repositioning an (already implanted) implant 2. To this end, the distal end 10-1 of the inner catheter shaft 10 may be guided to the implant 2. Then, the implant 2 may be attached to the holding element 101 by changing the shape of the shape memory element 1011.

For example, as illustrated in FIG. 6A, the holding element 101 may be introduced into a portion of the implant 2 while the shape memory element 1011 is in a state having a relatively small overall extension in the second direction Y. Then, the shape of the shape memory element 1011 may be changed by actuating the actuation element 102 so as to interlock the holding one with the implant 2 (see FIG. 6B). Finally, the holding element 101 may assume its usual holding state, thereby securing the implant 2 to the distal end 10-1 of the inner catheter shaft 10 (see FIG. 6C).

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantation catheter
10 First catheter shaft

10-1 Distal end of the first catheter shaft
101 Holding element
1011 Shape memory element
102 Actuation element
103 First lumen
104 Pushing element
12 Second catheter shaft
12-1 Distal end of the second catheter shaft
123 Second lumen
125 Protective sleeve
2 Implant
21 Fixation loops
3 Implantation catheter arrangement

The invention claimed is:

1. An implantation catheter, comprising:

an inner catheter shaft;

a holding element being arranged at a distal end of the inner catheter shaft and being configured for holding and releasing an implant;

an outer catheter shaft comprising a distal end with an enlarged lumen to form a protective sleeve which is configured for receiving the implant, wherein the holding element comprises a shape memory element, wherein the holding element is configured for assuming each of a holding state for holding the implant and a release state for releasing the implant, wherein a transition from the holding state to the release state and/or a transition from the release state to the holding state is supported by means of a shape memory of the shape memory element, wherein when the distal end of the inner catheter shaft points in a first direction, an overall extension of the holding element perpendicular to the first direction is larger in the holding state than in the release state, wherein in the holding state the overall extension of the holding element perpendicular to the first direction is larger than a corresponding extension of the implant, and wherein in the holding state, the holding element is configured for interlocking with one or more fixation elements.

2. The implantation catheter according to claim 1, wherein the shape memory element comprises a loop.

3. The implantation catheter according to claim 1, wherein the shape memory element comprises a nitinol wire.

4. The implantation catheter according to claim 1, wherein the inner catheter shaft comprises an actuation element that may be actuated at a proximal end of the inner catheter shaft for deforming the shape memory element.

5. The implantation catheter according to claim 4, wherein the actuation element extends inside a first lumen of the inner catheter shaft.

6. The implantation catheter according to claim 1, wherein a pushing element is arranged at the distal end of the inner catheter shaft, the pushing element being configured for pushing the implant out of the implantation catheter.

7. The implantation catheter according to claim 1, wherein the shape memory element is completely retracted in the inner catheter shaft while in the release state.

8. An implantation catheter arrangement, comprising:

an implantation catheter according to claim 1; and an implant being configured for interlocking with the holding element.

9. The implantation catheter arrangement according to claim 8, wherein the implant is a sensory implant or a therapeutic implant.

10. A method for handling an implant inside a human or animal body, wherein an implantation catheter arrangement according to claim 8 is used for at least one of the following:

implanting the implant;

explanting the implant; and repositioning the implant.

11. The method according to claim 10, further comprising the following steps:

a) guiding the implant to a desired implantation site while the implant is attached to the distal end of the inner catheter shaft by means of the holding element; and b) releasing the implant at the desired implantation site by changing the shape of the shape memory element.

12. The method according to claim 10, further comprising the following steps:

c) guiding the distal end of the inner catheter shaft to the implanted implant; and d) attaching the implant to the distal end of the inner catheter shaft by changing the shape of the shape memory element.

* * * * *